United States Patent [19]
Jonas et al.

[11] Patent Number: 5,378,702
[45] Date of Patent: Jan. 3, 1995

[54] THIADIZINONES

[75] Inventors: Rochus Jonas; Ingeborg Lues, both of Darmstadt; Klaus-Otto Minck, Ober-Ramstadt; Michael Klockow, Rossdorf, all of Germany

[73] Assignee: Merck Patent Gesellschaft Mit Beschrankter Haftung, Darmstadt, Germany

[21] Appl. No.: 89,485

[22] Filed: Jul. 16, 1993

[30] Foreign Application Priority Data

Jul. 17, 1992 [DE] Germany .................. 4223537

[51] Int. Cl.⁶ .................. C07D 417/02; A61K 31/54
[52] U.S. Cl. .................. 514/222.5; 514/213; 544/8; 540/593
[58] Field of Search .................. 544/8; 514/222.5, 213; 540/593

[56] References Cited
U.S. PATENT DOCUMENTS 4,916,128  4/1990  Jonas et al. .................. 514/213
5,137,885  8/1992  Jonas et al. .................. 514/222.5

Primary Examiner—John M. Ford
Attorney, Agent, or Firm—Millen, White, Zelano, & Branigan

[57] ABSTRACT

Thiadiazinones of the formula I

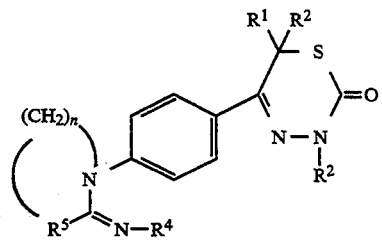

in which
$R^1$, $R^2$, $R^3$, $R^4$, $R^5$ and n have the meaning given in claim 1, show antiarrhythmic action and are suitable for the control of cardiovascular disorders.

18 Claims, No Drawings

THIADIZINONES

SUMMARY OF THE INVENTION

The invention relates to novel thiadiazinone derivatives of the formula I

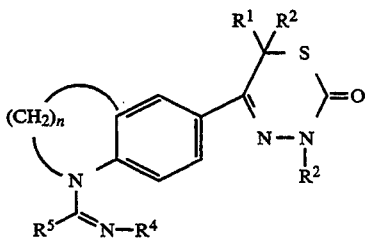

in which
R¹ and R² in each case independently of one another are H or A,
R³ is H, A or Ac,
R⁴ is H, A, cycloalkyl having 3-7 C atoms, Ar or Ar—alk,
R⁵ is Ar or Het,
A is alkyl having 1-8 C atoms,
Ac is A—CO—, At—CO—, Ar—alk—CO—, A—O—CO— or A—NH—CO—,
—alk is alkylene having 1-5 C atoms,
Ar is an unsubstituted phenyl radical or a phenyl radical which is mono-, di- or trisubstituted by A, OH, OA, F, Cl, Br, I, SA, SOA, SO₂A, NH₂, NHA, NA₂, NHAc, NHSO₂A, CN or NO₂,
Het is a saturated or unsaturated 5 - or 6-membered heterocyclic radical having 1-4 N, O and/or S atoms, which can be mono- or disubstituted by A, OA, F, Cl, Br, I, OH, NO₂, NH₂, NHA, NA₂, NHAc, NH—SO₂—A, SO—A, SO₂—A, SO₂NH₂ and/or SO₂NHA
and
n is 2, 3 or 4
and their salts.

Thiadiazinone derivatives whose basic structure corresponds to the formula (I), but which otherwise have a different substitution pattern, are disclosed in DE 37 19 031 A1, corresponding to U.S. Pat. No. 4,916,128.

The invention was based on the object of finding novel compounds having useful properties, in particular those which can be used for the production of medicaments.

It has been found that the compounds of the formula I have useful pharmacological properties together with good tolerability. In particular, they exhibit a potent antiarrhythmic action and a positively inotropic effect; the substances also have a vasodilating action and therefore promote circulation. The vasodilating action and the cardiac action can be determined, for example, in anaesthetized or conscious dogs, cats, monkeys or mini-pigs, and the positively inotropic action can also be determined on isolated heart preparations (for example auricle, papillary muscle or perfused whole heart) from rats, guinea-pigs, cats or dogs, for example by methods such as are described in Arzneimittelforschung, Volume 31 (I) No. 1a (1981), pages 141 to 170, or yon Schliep et al. in the 9th International Congress of Pharmacol., London, Abstracts of papers 9P (1984).

Antithrombotic properties, platelet aggregation-inhibiting properties and properties affecting the erythrocyte shape furthermore occur. The effect on the platelet function in the sense of an inhibition of aggregation can be detected on the rat ex vivo in the test according to Born (Nature 194, 927–929, 1962). The antithrombotic action is seen in the prolongation of the bleeding time according to Stella (Thrombos. Res. 7, 709–716, 1975), in the reduction of the thrombus weight in cold-induced thrombosis of the jugular vein in the rat according to Meng (Thor. Ber. 47, 69–79, 1975) and the increase in the laser pulses necessary for complete thrombosis on the mesenterial venules of the rat, corresponding to a modification of the method according to Kovacs (Microvasc. Res. 6, 194–201, 1973).

The favorable action on the erythrocyte deformability can be detected in a Nucleopore filter according to Schmid-Schönbein (Pflüger's Archiv 338, 93–114, 1973). Favourable effects on the fibrinolysis/euglobulin lysis time can also be determined according to v. Kaulla (Progr. Chem. Fibrinol., Thrombol. 1, 131–149, 1975; ed J. F. Davidson, Raven Press, N.Y.).

The compounds can therefore be used as pharmaceutical active substances in human and veterinary medicine. They can also be used as intermediates for the preparation of further pharmaceutical active substances.

The invention accordingly relates to the compounds of the formula I, their acid addition salts and a process for their preparation, characterized in that a compound of the formula II

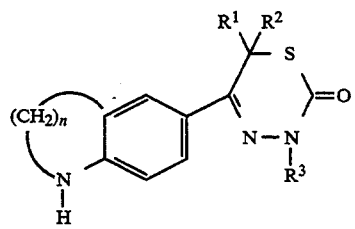

in which
R¹, R², R³ and n have the given meanings, is reacted with an imide chloride of the formula III

in which
R⁴ and R⁵ have the given meanings,
or in that a ketone of the formula IV

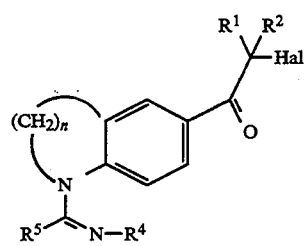

in which
R¹, R², R⁴, R⁵ and n have the given meanings and Hal is Cl, Br or I,
is reacted with a compound of the formula V

in which

R is alkyl having 1–5 C atoms or an equivalent of a metal or ammonium cation, e.g., Na+, K+, or NH4+, or in that, to prepare a compound of the formula I in which R⁴ is H, a corresponding compound, which, however, instead of R⁴ carries an amino-protective group, is treated with a hydrolyzing or hydrogenolyzing agent, or in that, to prepare a compound of the formula I in which R⁴ is H, a halomagnesium compound of the formula VI

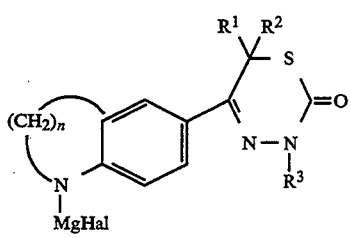

in which
R¹, R², R³, Hal and n have the given meanings, is reacted with a nitrile of the formula VII

in which
R⁵ has the given meaning, and the product obtained is then hydrolyzed,
or in that a compound of the formula VIII

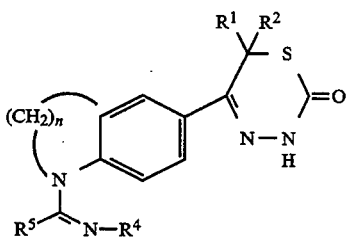

in which
R¹, R², R⁴, R⁵ and n have the given meanings, is reacted with an acyl or alkyl derivative of the formula IX

in which
R³′ is A or Ac and
Hal has the previously given meaning,
or in that, if desired, in a thiadiazinone derivative of the formula I, one or both radicals R⁴ and/or R⁵ are converted into (an) other radical(s) R⁴ and/or R⁵ and/or a base of the formula I obtained is converted by treatment with an acid into one of its acid addition salts.

Above and below, R¹, R², R³, R⁴, R⁵, n, Hal and R have the meanings given in the formulae I, IV or V, if not expressly stated otherwise.

In the formulae, A is alkyl radicals having 1–8 C atoms, which are preferably unbranched and preferably contain 1, 2, 3, 4 or 5 C atoms, preferably methyl, also preferably ethyl or propyl, furthermore preferably isopropyl, butyl, isobutyl, sec-butyl, tert-butyl, n-pentyl or isopentyl.

The radical Ar can be unsubstituted phenyl, but is preferably monosubstituted or disubstituted phenyl, where the substituents can be identical or different and are preferably in the para- or in the para- and meta-position. Particularly preferred substituents are methoxy, chlorine, NO2, CN and NHSO2CH3, but also hydroxyl, alkylthio, alkylsulfinyl, alkylsulfonyl and ethoxy.

In detail, Ar is preferably phenyl, p-nitrophenyl, p-cyanophenyl, p-methanesulfonamidophenyl, p-chlorophenyl, p-methoxyphenyl or 3,4-dimethoxyphenyl.

The group "—alk" is a straight-chain or branched alkylene group, preferably —CH2— or —CH2—CH2—.

Cycloalkyl can contain 3–7 C atoms, but preferably contains 5 or 6 C atoms and is preferably cyclopentyl or cyclohexyl.

The radicals R¹, R² and R³ are preferably in each case H or methyl.

R³ is also preferably A—CO—, Ar—CO—, Ar—alk—CO—, A—O—CO— or A—NH—CO—, in which A, "—alk" and Ar have the preferred meanings already given.

The radical R⁴ is preferably ethyl, furthermore preferably phenyl, benzyl or 2-phenylethyl, but also cyclopentyl, methyl, propyl, isopropyl, butyl or isopentyl.

The radical R⁵ is preferably phenyl, particularly preferably substituted phenyl, preferably p-nitrophenyl, p-methanesulfonamidophenyl, p-cyanophenyl, p-chlorophenyl, p-methoxyphenyl or 3,4-dimethoxyphenyl, also preferably 2-thienyl or 2-, 3- or 4-pyridyl.

The invention relates in particular to those compounds of the formula I in which at least one of the said radicals has one of the preferred meanings given above.

Some preferred groups of compounds can be expressed by the following sub-formulae Ia to If, which correspond to the formula I and in which the radicals which are not described in greater detail have the meanings given under the formula I, but in which in Ia the dihydrothiadiazinone ring is in the 6-position of a 1,2,3,4-tetrahydroquinoline,
  R¹, R² and R³ are in each case independently of one another H or methyl,
  R⁴ is alkyl having 1–5 C atoms and
  R⁵ is monosubstituted or disubstituted phenyl;
in Ib the dihydrothiadiazinone ring is in the 6-position of a 1,2,3,4-tetrahydroquinoline,
  R¹, R² and R³ are in each case independently of one another H or methyl,
  R⁴ is phenyl and
  R⁵ is monosubstituted or disubstituted or unsubstituted phenyl;
in Ic the dihydrothiadiazinone ring is in the 6-position of a 1,2,3,4-tetrahydroquinoline,
  R¹, R² and R³ are in each case independently of one another H or methyl:
  R⁴ is ethyl and
  R⁵ is monosubstituted or disubstituted phenyl;
in Id the dihydrothiadiazinone ring is in the 6-position of a 1,2,3,4-tetrahydroquinoline,
  R¹, R² and R³ are in each case independently of one another H or methyl,
  R⁴ is alkyl having 1–5 C atoms and
  R⁵ is phenyl, p-nitrophenyl, p-cyanophenyl, p-methanesulfonamidophenyl, p-chlorophenyl, p-methoxyphenyl, 3,4-dimethoxyphenyl or 2-thienyl;
in Ie the dihydrothiadiazinone ring is in the 6-position of a 1,2,3,4-tetrahydroquinoline, $R^1$, $R^2$ and $R^3$ are in each case independently of one another H or methyl, $R^4$ is benzyl or 2-phenylethyl and $R^5$ is phenyl, p-nitrophenyl, p-cyanophenyl, p-methanesulfonamidophenyl, p-chlorophenyl, p-methoxyphenyl, 5 3,4-dimethoxyphenyl or 2-thienyl;

in If the dihydrothiadiazinone ring is in the 6-position of a 1,2,3,4-tetrahydroquinoline, $R^1$, $R^2$ and $R^3$ are in each case independently of one another H or methyl, $R^4$ is ethyl and $R^5$ is 2-thienyl, p-nitrophenyl, p-cyanophenyl or p-methanesulfonamidophenyl.

The compounds of the formula I are otherwise prepared by methods known per se, such as are described in the literature (for example in the standard works such as Houben-Weyl, Methoden der Organischen Chemie (Methods of Organic Chemistry), Georg-Thieme-Verlag, Stuttgart), namely under reaction conditions which are known and suitable for the said reactions. Use can also be made in this case of variants which are known per se and not mentioned in greater detail here.

If desired, the starting substances for the claimed process can also be formed in situ in such a way that they are not isolated from the reaction mixture, but immediately reacted further to give the compounds of the formula I.

The starting substances of the formulae II and III are known in some cases. If they are not known, they can be prepared by methods known per se. The preparation of the compounds of the formula II is disclosed in DE 37 19 031, corresponding to U.S. Pat. No. 4,916,128.

In detail, the reaction of the compounds of the formula II with the compounds of the formula III is carried out in the presence or absence of an inert solvent at temperatures between about $-20°$ and about $+150°$, preferably between 20° and 100°. Suitable solvents are, for example, hydrocarbons such as benzene, toluene, xylenes or mesitylene; halogenated hydrocarbons such as dichloromethane, trichloroethylene or chlorobenzene; alcohols such as methanol, ethanol or isopropanol; glycols or glycol ethers such as ethylene glycol, diethylene glycol, 2-methoxyethanol; nitriles such as acetonitrile; ethers such as tetrahydrofuran or dioxane; amides such as dimethylformamide (DMF); and sulfoxides such as dimethyl sulfoxide. Mixtures of these solvents are also suitable.

In the compounds of the formula IV, Hal is preferably Cl or Br.

In the compounds of the formula V, R is preferably methyl or ethyl, but also $Na^+$, $K^+$ or $NH_4^+$.

If desired, these starting substances can also be formed in situ in such a way that they are not isolated from the reaction mixture, but immediately reacted further to give the compounds of the formula I. On the other hand, it is possible to carry out the reaction stepwise, in which case further intermediates can be isolated.

The starting substances of the formulae IV and V are known in some cases. If they are not known, they can be prepared by methods known per se. The ketones of the formula IV are accessible, for example, by Friedel-Crafts synthesis from corresponding tetrahydroquinoline derivatives using compounds of the formula Hal—CO—$CHR^2$—Hal.

In detail, the reaction of the ketones of the formula IV with the compounds of the formula V is carried out under conditions that have been given beforehand for the reaction between compounds of the formulae II and III.

A compound of the formula I can also be obtained by treating a compound which otherwise corresponds to the formula I, but instead of $R^4$ carries an "amino protective group", with a reagent which reductively removes this "protective group".

"Protective groups" used are preferably CO$_2$—$CH_2C_6H_5$, particularly preferably OH, which can preferably be removed by transition metal carbonyls, particularly preferably by iron pentacarbonyl, but also by $Fe_2(CO)_9$ at temperatures between about $-20°$ and about $+150°$, preferably between 20° and 100°, in the presence or absence of an inert solvent.

Suitable solvents are, for example, those given above for the reaction of II with III.

Compounds of the formula I can also be obtained by reacting a halomagnesium compound of the formula VI with a nitrile of the formula VII and then hydrolyzing the product obtained.

Compounds of the formulae VI and VII are known or can be prepared by methods known per se.

These reactions preferably take place under conditions such as are known for Grignard reactions or other organometallic reactions, expediently in the presence or absence of an inert solvent at temperatures between about $-20°$ and about $+150°$, preferably between 0° and 150°. Suitable solvents are those given above, if they cannot themselves react with the compounds of the formula VI.

A compound of the formula I can furthermore also be obtained by reacting a compound of the formula VIII with an alkyl or acyl derivative of the formula IX.

Compounds of the formula VIII are known and can be prepared in analogy to the compounds described in DE 40 41 074 A1.

The alkyl and acyl derivatives of the formula IX are also known. These compounds can be prepared by simple organic-chemical synthesis procedures such as are described, for example, in J. March, Adv. Org. Chem., 3rd Ed., J. Wiley & Sons New York (1985).

The reactions of the two compounds preferably take place under conditions such as are known for the alkylation and acylation of primary and secondary amines. It is expedient to carry out the reactions in the presence or absence of an inert solvent, at temperatures between about $-10°$ and about $+180°$, preferably between 0° and 150°. Suitable solvents are those given beforehand, if these cannot participate in the reaction themselves.

It is also possible to convert one or both radical(s) $R^4$ and/or $R^5$ into (an)other radical(s) $R^4$ and/or $R^5$. For example, using reactions known per se, an $NO_2$ group can be reduced to an $NH_2$ group, an $NH_2$ or NHA group can be alkylated, an OH group can be etherified or else an aryl ether can be cleaved. In addition, substituents of these radicals $R^4$ and/or $R^5$, such as, for example, S—$R^6$ or SO—$R^6$ groups, can be oxidized if the reactions take place selectively on the radicals $R^4$ and/or $R^5$.

A base of the formula I can be converted into the respective acid addition salt using an acid. Suitable acids for this reaction are in particular those which give physiologically acceptable salts. Inorganic acids can thus be used, for example sulfuric acid, nitric acid, hydrohalic acids such as hydrochloric acid or hydrobromic acid, phosphoric acids such as orthophosphoric acid, sulfamic acid, also organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- and ethanesulfonic acid, ethanedisulfonic acid, 2-hydroxyethanesulfonic acid, benzenesulfonic acid, p-toluenesulfonic acid, naphthalenemono- and disulfonic acids, and laurylsulfuric acid. Salts with physiologically unacceptable acids, for example picrates, can be used for purifying the compounds of the formula I.

Compounds of the formula I can contain one or more asymmetric centers. In this case, they usually exist in racemic form. The racemates obtained can be resolved mechanically or chemically into their optical antipodes by methods known per se. Diastereomers are preferably formed from the racemic mixture by reaction with an optically active resolving agent. Suitable resolving agents for basic compounds of the formula I are, for example, optically active acids, such as the D- and L-forms of tartaric acid, diacetyltartaric acid, dibenzoyltartaric acid, mandelic acid, malic acid, lactic acid or the various optically active camphorsulfonic acids, such as β-camphorsulfonic acid or else optically active camphanic acid or other optically active terpene acids.

Of course, it is also possible to obtain optically active compounds of the formula I by the methods described above by using starting substances which are already optically active.

Moreover, the compounds of the formula I, in analogy to the E/Z isomerism in the case of C=C double bonds, show a comparable stereoisomerism of the non-cyclic C=N double bond. The compounds can thus exist as mixtures of the possible stereoisomers or else as pure E- or Z-isomers.

The invention also relates to the use of the compounds of the formula I and their physiologically acceptable salts for the production of pharmaceutical preparations, in particular in non-chemical ways. In this process, they can be brought into a suitable dose form together with at least one solid, liquid and/or semi-liquid excipient or auxiliary and, if appropriate, in combination with one or more other active substances.

The invention also relates to compositions, in particular pharmaceutical preparations, containing at least one compound of the formula I and/or one of its physiologically acceptable salts.

These preparations can be used as medicaments in human or veterinary medicine. Suitable excipients are organic or inorganic substances which are suitable for enteral (for example oral), parenteral or topical application and do not react with the novel compounds, for example water, vegetable oils, benzyl alcohols, polyethylene glycols, glycerol triacetate, gelatine, carbohydrates such as lactose or starch, magnesium stearate, talc and petroleum jelly. Tablets, coated tablets, capsules, syrups, juices or drops are used in particular for oral administration, suppositories for rectal administration, solutions, preferably oily or aqueous solutions, also suspensions, emulsions or implants for parenteral administration, and ointments, creams, sticks or powders for topical application. The novel compounds can also be lyophilized and the lyophilizates obtained used, for example, for the production of injection preparations.

The given preparations can be sterilized and/or contain auxiliaries such as lubricants, preservatives, stabilizers and/or wetting agents, emulsifiers, salts for affecting the osmotic pressure, buffer substances, colorants, flay and/or aromatizers. If desired, they can also contain one or more further active substances, for example one or more vitamins.

The compounds of the formula I can be used in the control of diseases, in particular of arrhythmias and of cardiac insufficiency and in the therapeutic treatment of the human or animal body.

In this case, the substances according to the invention are as a rule administered in analogy to known substances having positively inotropic activity such as amrinone, preferably in doses between about 1 and 100 mg, in particular between 2 and 20 mg per dose unit.

The daily dose is preferably between about 0.02 and 2 mg/kg of body weight. The specific dose for each specific patient depends, however, on the most diverse factors, for example on the activity of the specific compound employed, on the age, body weight, general state of health, sex, on the diet, on the time and route of administration, on the excretion rate, medicament combination and severity of the particular disorder to which the therapy applies. Oral administration is preferred. In comparison to the digitalis glycosides previously used for the therapy of cardiac insufficiency, the compounds of the formula I are distinguished by improved therapeutic breadth and peripheral relief.

In the following examples, "customary working up" means:

If necessary, water or dilute sodium hydroxide solution is added, the mixture is extracted with an organic solvent such as ethyl acetate, chloroform or dichloromethane, the organic phase is separated off, dried over sodium sulfate, filtered and evaporated, and the residue is purified by chromatography and/or crystallization.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 42 23 537.5, are hereby incorporated by reference.

EXAMPLES

Example 1

A solution of 2.6 g of 5-(1,2,3,4-tetrahydroquinolin-6-yl)-6,6-dimethyl-3,6-dihydro-1,3,4-thiadiazin-2-one ("A") [obtainable from O-ethyl hydrazinothioformate and 6-(2-chloro-2-methylpropionyl)-2-oxo-1,2,3,4-tetrahydroquinoline] in 40 ml of dichloromethane and 1 ml of pyridine is treated with 2.1 g of N-ethyl-3,4-dimethoxybenzimidoyl chloride [obtainable from N-ethyl-3,4-dimethoxybenzamide by reaction with thionyl chloride] dissolved in 20 ml of dichloromethane with ice-cooling and the mixture is stirred for 1 hour. After removal of the solvent, the mixture is worked up in the customary manner and 5-[1-(N-ethyl-3,4-dimethoxybenzimidoyl)-1,2,3,4-tetrahydroquinolin-6-yl]-6,6- dimethyl-3,6-dihydro-2H-1,3,4-thiadiazin-2-one, m.p. 188°, is obtained.

The following are obtained analogously:

starting from "A" by reaction with N-ethyl-p-methoxybenzimidoyl chloride: 5-[1-(N-ethyl-p-methoxybenzimidoyl)-1,2,3,4-tetrahydroquinolin-6-yl]-6,6-dimethyl-3,6-dihydro-2H-1,3,4-thiadiazin-2-one, m.p. 244° (hydrochloride);

with N-phenyl-p-methoxybenzimidoyl chloride: 5-[1-(N-phenyl-p-methoxybenzimidoyl)-1,2,3,4-tetrahydroquinolin-6-yl]-6,6-dimethyl-3,6-dihydro-2H-1,3,4-thiadiazin-2-one, m.p. 210° (hydrochloride);

with N-ethyl-p-chlorobenzimidoyl chloride: 5-[1-(N-ethyl-p-chlorobenzimidoyl)-1,2,3,4-tetrahydroquinolin-6-yl]-6,6-dimethyl-3,6-dihydro-2H-1,3,4-thiadiazin-2-one, m.p. 254° (hydrochloride);

with N-ethyl-2-thienylimidoyl chloride: 5-[1-(N-ethyl-2-thienylimidoyl)-1,2,3,4-tetrahydroquinolin-6-yl]-6,6-dimethyl-3,6-dihydro-2H-1,3,4-thiadiazin-2-one, m.p. 223° (hydrochloride);

with N-(2-phenylethyl)-p-methoxybenzimidoyl chloride: 5-[1-(N-(2-phenylethyl-p-methoxybenzimidoyl)-1,2,3,4-tetrahydroquinolin-6-yl]-6,6-dimethyl-3,6-dihydro-2H-1,3,4-thiadiazin-2-one, m.p. 245° (hydrochloride);

with N-ethyl-o-methoxybenzimidoyl chloride: 5-[1-(N-ethyl-o-methoxybenzimidoyl)-1,2,3,4-tetrahydroquinolin-6-yl]-6,6-dimethyl-3,6-dihydro-2H-1,3,4-thiadiazin-2-one;

with N-ethyl-m-methoxybenzimidoyl chloride: 5-[1-(N-ethyl-m-methoxybenzimidoyl)-1,2,3,4-tetrahydroquinolin-6-yl]-6,6-dimethyl-3,6-dihydro-2H-1,3,4-thiadiazin-2-one;

with N-ethyl-2,4-dimethoxybenzimidoyl chloride: 5-[1-(N-ethyl-2,4-dimethoxybenzimidoyl)-1,2,3,4-tetrahydroquinolin-6yl]-6,6-dimethyl-3,6-dihydro-2H-1,3,4-thiadiazin-2-one;

with N-methyl-p-methoxybenzimidoyl chloride: 5-[(1-(N-methyl-p-methoxybenzimidoyl)-1,2,3,4-tetrahydroquinolin-6-yl]-6,6-dimethyl-3,6-dihydro-2H-1,3,4-thiadiazin-2-one;

with N-ethyl-3,4-dichlorobenzimidoyl chloride: 5-[1-(N-ethyl-3,4-dichlorobenzimidoyl)-1,2,3,4-tetrahydroquinolin-6-yl]-6,6-dimethyl-3,6-dihydro-2H-1,3,4-thiadiazin-2-one;

with N-ethyl-2,4-dichlorobenzimidoyl chloride: 5-[1-(N-ethyl-2,4-dichlorobenzimidoyl)-1,2,3,4-tetrahydroquinolin-6-yl]-6,6-dimethyl-3,6-dihydro-2H-1,3,4-thiadiazin-2-one;

with N-isopropyl-p-methoxybenzimidoyl chloride: 5-[1-(N-isopropyl-p-methoxybenzimidoyl)-1,2,3,4-tetrahydroquinolin-6-yl]-6,6-dimethyl-3,6-dihydro-2H-1,3,4-thiadiazin-2-one;

with N-cyclohexyl-p-methoxybenzimidoyl chloride: 5-[1-(N-cyclohexyl-p-methoxybenzimidoyl)-1,2,3,4-tetrahydroquinolin-6-yl]-6,6-dimethyl-3,6-dihydro-2H-1,3,4-thiadiazin-2-one;

with N-isopropyl-p-chlorobenzimidoyl chloride: 5-[1-(N-isopropyl-p-chlorobenzimidoyl)-1,2,3,4-tetrahydroquinolin-6-yl]-6,6-dimethyl-3,6-dihydro-2 H-1,3,4-thiadiazin-2-one;

with N-isopropyl-2-thienylimidoyl chloride: 5-[1-(N-isopropyl-2-thienylimidoyl)-1,2,3,4-tetrahydroquinolin-6-yl]-6,6-dimethyl-3,6-dihydro-2H-1,3,4-thiadiazin-2-one;

with N-benzyl-p-methoxybenzimidoyl chloride: 5-[1-(N-benzyl-p-methoxybenzimidoyl)-1.2,3,4-tetrahydroquinolin-6-yl]-6,6-dimethyl-3,6-dihydro-2H-1,3,4-thiadiazin-2-one;

with N-isopropyl-o-methoxybenzimidoyl chloride: 5-[1-(N-isopropyl-o-methoxybenzimidoyl)-1,2,3,4-tetrahydroquinolin-6-yl]-6,6-dimethyl-3,6-dihydro-2H-1,3,4-thiadiazin-2-one;

with N-isopropyl-m-methoxybenzimidoyl chloride: 5-[1-(N-isopropyl-m-methoxybenzimidoyl)-1,2,3,4-tetrahydroquinolin-6-yl]-6,6-dimethyl-3,6-dihydro-2H-1,3,4-thiadiazin-2-one;

with N-isopropyl-2,4-dimethoxybenzimidoyl chloride: 5-[1-(N-isopropyl-2,4-dimethoxybenzimidoyl)-1,2,3,4-tetrahydroquinolin-6-yl]-6,6-dimethyl-3,6-dihydro-2H-1,3,4-thiadiazin-2-one;

with N-cyclohexyl-p-methoxybenzimidoyl chloride: 5-[1-(N-cyclohexyl-p-methoxybenzimidoyl)-1,2,3,4-tetrahydroquinolin-6-yl]-6,6-dimethyl-3,6-dihydro-2H-1,3,4-thiadiazin-2-one;

p0 with N-isopropyl-3,4-dichlorobenzimidoyl chloride: 5-[1-(N-isopropyl-3,4-dichlorobenzimidoyl)-1,2,3,4-tetrahydroquinolin-6-yl]-6,6-dimethyl-3,6-dihydro-2H-1, 3,4-thiadiazin-2-one;

with N-isopropyl-2,4-dichlorobenzimidoyl chloride: 5-[1- (N-isopropyl-2,4-dichlorobenzimidoyl)-1,2,3,4-tetrahydroquinolin-6-yl]-6,6-dimethyl-3,6-dihydro-2H-1,3,4-thiadiazin-2-one.

Example 2

5-[1-N-Hydroxy-3,4-dimethoxybenzimidoyl)-1,2,3,4-tetrahydroquinolin-6-yl]-6,6-dimethyl-3,6-dihydro-2H-1,3,4-thiadiazin-2-one is obtained analogously to Example 1 starting from "A" by reaction, with N-hydroxy-3,4-dimethoxybenzimidoyl chloride.

The following are obtained analogously:

starting from "A" by reaction with N-hydroxy-p-methoxybenzimidoyl chloride: 5-[1-(N-hydroxy-p-methoxybenzimidoyl)-1,2,3,4-tetrahydroquinolin-6-yl]-6,6-dimethyl-3,6-dihydro-2H-1,3,4-thiadiazin-2-one;

with N-hydroxy-p-fluorobenzimidoyl chloride: 5-[1-(N-hydroxy-p-fluorobenzimidoyl)-1,2,3,4-tetrahydroquinolin-6-yl]-6,6-dimethyl-3,6-dihydro-2H-1,3,4-thiadiazin-2-one;

with N-hydroxy-p-chlorobenzimidoyl chloride: 5-[1-(N-hydroxy-p-chlorobenzimidoyl)-1,2,3,4-tetrahydroquinolin-6-yl]-6,6-dimethyl-3,6-dihydro-2H-1,3,4-thiadiazin-2-one;

with N-hydroxy-p-methylthiobenzimidoyl chloride: 5-[1-(N-hydroxy-p-methylthiobenzimidoyl)-1,2,3,4-tetrahydroquinolin-6-yl]-6,6-dimethyl-3,6-dihydro-2H-1,3,4-thiadiazin-2-one;

with N-hydroxy-o-methoxybenzimidoyl chloride: 5-[1-(N-hydroxy-o-methoxybenzimidoyl)-1,2,3,4-tetrahydroquinolin-6-yl]-6,6-dimethyl-3,6-dihydro-2H-1,3,4-thiadiazin-2-one;

with N-hydroxy-m-methoxybenzimidoyl chloride: 5-[1-(N-hydroxy-m-methoxybenzimidoyl)-1,2,3,4-tetrahydroquinolin-6-yl]-6,6-dimethyl-3,6-dihydro-2H-1,3,4-thiadiazin-2-one;

with N-hydroxy-2,4-dimethoxybenzimidoyl chloride: 5-[1-(N-hydroxy-2,4-dimethoxybenzimidoyl)-1,2,3,4-tetrahydroquinolin-6-yl]-6,6-dimethyl-3,6-dihydro-2H-1,3,4-thiadiazin-2-one;

with N-hydroxy-p-methylsulfonylbenzimidoyl chloride: 5-[1-(N-hydroxy-p-methylsulfonylbenzimidoyl)-1,2,3,4-tetrahydroquinolin-6-yl]-6,6-dimethyl-3,6-dihydro-2H-1,3,4-thiadiazin-2-one;

with N-hydroxy-3,4-dichlorobenzimidoyl chloride: 5-[1-(N-hydroxy-3,4-dichlorobenzimidoyl)-1,2,3,4-tetrahydroquinolin-6-yl]-6,6-dimethyl-3,6-dihydro-2H-1,3,4-thiadiazin-2-one;

with N-hydroxy-2,4-dichlorobenzimidoyl chloride: 5-[1-(N-hydroxy-2,4-dichlorobenzimidoyl)-1,2,3,4-tetrahydroquinolin-6-yl]-6,6-dimethyl-3,6-dihydro-2H-1,3,4-thiadiazin-2-one;

with N-hydroxy-p-ethylthiobenzimidoyl chloride: 5-[1-(N-hydroxy-p-ethylthiobenzimidoyl-1,2,3,4-tetrahydroquinolin-6-yl]-6,6-dimethyl-3,6-dihydro-2H-1,3,4-thiadiazin-2-one;

with N-hydroxy-p-methylsulfinylbenzimidoyl chloride: 5-[1-(N-hydroxy-p-methylsulfinylbenzimidoyl)-1,2,3,4-tetrahydroquinolin-6-yl]-6,6-dimethyl-3,6-dihydro-2H-1,3,4-thiadiazin-2-one;

with N-hydroxy-p-nitrobenzimidoyl chloride: 5-[1-(N-hydroxy-p-nitrobenzimidoyl)-1,2,3,4-tetrahydroquinolin-6-yl]-6,6-dimethyl-3,6-dihydro-2H-1,3,4-thiadiazin-2-one;

with N-hydroxy-(p-N-dimethylamino)benzimidoyl chloride: 5-[1-(N-hydroxy-(p-N-dimethylamino)benzimidoyl)-1,2,3,4-tetrahydroquinolin-6-yl]-6,6-dimethyl-3,6-dihydro-2H-1,3,4-thiadiazin-2-one;

with N-hydroxy-p-acetamidobenzimidoyl chloride: 5-[1-(N-hydroxy-p-acetamidobenzimidoyl)-1,2,3,4-tetrahydroquinolin-6-yl]-6,6-dimethyl-3,6-dihydro-2H-1,3,4-thiadiazin-2-one;

with N-hydroxy-p-methanesulfonamidobenzimidoyl chloride: 5-[1-(N-hydroxy-p-methanesulfonamidobenzimidoyl)-1,2,3,4-tetrahydroquinolin-6-yl]-6,6-dimethyl-3,6-dihydro-2H-1,3,4-thiadiazin-2-one;

with N-hydroxy-3,4-dinitrobenzimidoyl chloride: 5-[1-(N-hydroxy-3,4-dinitrobenzimidoyl)-1,2,3,4-tetrahydroquinolin-6-yl]-6,6-dimethyl-3,6-dihydro-2H-1,3,4-thiadiazin-2-one.

Example 3

1 equivalent of iron pentacarbonyl is added dropwise to a solution of 3.4 g of 5-[1-N-hydroxy-3,4-dimethoxybenzimidoyl)-1,2,3,4-tetrahydroquinolin-6-yl]-6,6-dimethyl-3,6-dihydro-2H-1,3,4-thiadiazin-2-one in 30 ml of tetrahydrofuran. The reaction mixture is boiled for 2 hours and worked up in the customary manner. 5-[1-(3,4-dimethoxybenzimidoyl)-1,2,3,4-tetrahydroquinolin-6-yl]-6,6-dimethyl-3,6-dihydro-2H-1,3,4-thiadiazin-2-one is obtained.

The following are obtained analogously from the corresponding N-hydroxybenzimidoyl derivatives:

5-[1-(p-methoxybenzimidoyl)-1,2,3,4-tetrahydroquinolin-6-yl]-6,6-dimethyl-3,6-dihydro-2H-1,3,4-thiadiazin-2-one;

5-[1-(p-fluorobenzimidoyl)-1,2,3,4-tetrahydroquinolin-6-yl]-6,6-dimethyl-3,6-dihydro-2H-1,3,4-thiadiazin-2-one;

5-[1-(p-chlorobenzimidoyl)-1,2,3,4-tetrahydroquinolin-6-yl]-6,6-dimethyl-3,6-dihydro-2H-1,3,4-thiadiazin-2-one;

5-[1-(p-methylthiobenzimidoyl)-1.2,3,4-tetrahydroquinolin-6-yl]-6,6-dimethyl-3,6-dihydro-2H-1,3,4-thiadiazin-2-one;

5-[1-(o-methoxybenzimidoyl)-1,2,3,4-tetrahydroquinolin-6-yl]-6,6-dimethyl-3,6-dihydro-2H-1,3,4-thiadiazin-2-one;

5-[1-(m-methoxybenzimidoyl)-1,2,3,4-tetrahydroquinolin-6-yl]-6,6-dimethyl-3,6-dihydro-2H-1,3,4-thiadiazin-2-one;

5-[1-(2,4-dimethoxybenzimidoyl)-1,2,3,4-tetrahydroquinolin-6-yl]-6,6-dimethyl-3,6-dihydro-2H-1,3,4-thiadiazin-2-one;

5-[1-(p-methylsulfonylbenzimidoyl)-1,2,3,4-tetrahydroquinolin-6-yl]-6,6-dimethyl-3,6-dihydro-2H-1,3,4-thiadiazin-2-one;

5-[1-(3,4-dichlorobenzimidoyl)-1,2,3,4-tetrahydroquinolin-6-yl]-6,6-dimethyl-3,6-dihydro-2H-1,3,4-thiadiazin-2-one;

5-[1-(2,4-dichlorobenzimidoyl)-1,2,3,4-tetrahydroquinolin-6-yl]-6,6-dimethyl-3,6-dihydro-2H-1,3,4-thiadiazin-2-one;

5-[1-(p-ethylthiobenzimidoyl)-1,2,3,4-tetrahydroquinolin-6-yl]-6,6-dimethyl-3,6-dihydro-2H-1,3,4-thiadiazin-2-one;

5-[1-(p-methylsulfinylbenzimidoyl)-1,2,3,4-tetrahydroquinolin-6-yl]-6,6-dimethyl-3,6-dihydro-2H-1,3,4thiadiazin-2-one;

5-[1-(p-nitrobenzimidoyl)-1,2,3,4-tetrahydroquinolin-6-yl]-6,6-dimethyl-3,6-dihydro-2H-1,3,4,5-thiadiazin-2-one;

5-[1-(p-(N,N-dimethylaminobenzimidoyl)-1,2,3,4-tetrahydroquinolin-6-yl]-6,6-dimethyl-3,6-dihydro-2H-1,3,4-thiadiazin-2-one;

5-[1-(p-acetamidobenzimidoyl)-1,2,3,4-tetrahydroquinolin-6-yl]-6,6-dimethyl-3,6-dihydro-2H-1,3,4-thiadiazin-2-one;

5-[1-(o-acetamidobenzimidoyl)-1,2,3,4-tetrahydroquinolin-6-yl]-6,6-dimethyl-3,6-dihydro-2H-1,3,4-thiadiazin-2-one;

5-[1-(p-methanesulfonamidobenzimidoyl)-1,2,3,4-tetrahydroquinolin-6-yl]-6,6-dimethyl-3,6-dihydro-2H-1,3,4-thiadiazin-2-one;

5-[1-(3,4-dinitrobenzimidoyl)-1,2,3,4-tetrahydroquinolin-6-yl]-6,6-dimethyl-3,6-dihydro-2H-1,3,4-thiadiazin-2-one.

Example 4

A solution of 1.7 g of 1-(N-ethyl-p-methoxybenzimidoyl)-6-(2-chloro-2-methylpropionyl)-1,2,3,4-tetrahydroquinoline in 40 ml of acetonitrile is treated with 1 equivalent of O-ethyl hydrazinothioformate and the mixture is boiled for 2 hours. After customary working up, 5-[1-(N-ethyl-p-methoxybenzimidoyl)-1,2,3,4-tetrahydroquinolin-6-yl]-6,6-dimethyl-3,6-dihydro-2H-1,3,4-thiadiazin-2-one, m.p. 244° (hydrochloride), is obtained.

The following are obtained analogously by reaction of O-ethyl hydrazinothioformate with 1-(N-benzyl-p-methoxybenzimidoyl)-6-(2-chloro-2-methylpropionyl)-1,2,3,4-tetrahydroquinoline: 5-[1-N-benzyl-p-methoxybenzimidoyl)-1,2,3,4-tetrahydroquinolin-6-yl]-6,6-dimethyl-3,6-dihydro-2H-1,3,4-thiadiazin-2-one;

with 1-(N-cyclopentyl-p-methoxybenzimidoyl)-6-(2-chloro-2-methylpropionyl)-1,2,3,4-tetrahydroquinoline: 5-[1-N-cyclopentyl-p-methoxybenzimidoyl)-1,2,3,4-tetrahydroquinolin-6-yl]-6,6-dimethyl-3,6-dihydro-2H-1,3,4-thiadiazin-2-one;

with 1-(N-cyclohexyl-p-methoxybenzimidoyl)-6-(2-chloro-2-methylpropionyl)-1,2,3,4-tetrahydroquinoline: 5-[1-N-cyclohexyl-p-methoxybenzimidoyl)-1,2,3,4-tetrahydroquinolin-6-yl]-6,6-dimethyl-3,6-dihydro-2H-1,3,4 -thiadiazin-2-one;

with 1-(N-(2-phenylethyl)-p-methoxybenzimidoyl)-6-(2-chloro-2-methylpropionyl)-1,2,3,4-tetrahydroquinoline: 5-[1-N-(2-phenylethyl)-p-methoxybenzimidoyl)-1,2,3,4-tetrahydroquinolin-6-yl]-6,6-dimethyl-3,6-dihydro-2H-1,3,4-thiadiazin-2-one;

with 1-(N-(2-phenylethyl)-3,4-dimethoxybenzimidoyl)-6-(2-chloro-2-methylpropionyl)-1,2,3,4-tetrahydroquinoline: 5-[1-N-(2-phenylethyl)-3,4-dimethoxybenzimidoyl)-1,2,3,4-tetrahydroquinolin-6-yl]-6,6-dimethyl-3,6-dihydro-2H-1,3,4-thiadiazin-2-one.

Example 5

A solution of 1.2 g of 6-(6,6-dimethyl-2-oxo-3,6-dihydro-2H-1,3,4-thiadiazin-5-yl)-1,2,3,4-tetrahydroquinoline-1-magnesium bromide ("B") in 40 ml of tetrahydrofuran is treated dropwise with one equivalent of p-chlorobenzonitrile and the mixture is boiled for 1.5 hours. After customary working up 5-[1-(p-chlorobenzimidoyl)-1,2,3,4-tetrahydroquinolin-6-yl]-6,6-dimethyl-3,6-dihydro-2H-1,3,4-thiadiazin-2-one is obtained.

Example 6

A solution of 2.8 g of 5-[1-N-ethyl-3,4-dimethoxybenzimidoyl)-1,2,3,4-tetrahydroquinolin-6-yl]-6,6-dimethyl-3,6-dihydro-2H-1,3,4-thiadiazin-2-one (m.p. 188°) in 40 ml of dimethylformamide is treated with ice-cooling with 0.3 g of NaH and the mixture is stirred for 1 hour. 1.5 ml of ethyl iodide are then added, the mixture is stirred fur a further 2 hours and, after customary working up, 5-[1-N-ethyl-3,4-dimethoxybenzimidoyl)-1,2,3,4-tetrahydroquinolin-6-yl]-3-ethyl-6,6-dimethyl-3,6-dihydro-2H-1,3,4-thiadiazin-2-one is obtained.

The following are obtained analogously by alkylation of the corresponding compounds of the formula I in the 3-position of the thiadiazinone system:

5-[1-(N-ethyl-p-methoxybenzimidoyl)-1,2,3,4-tetrahydroquinolin-6-yl]-3-ethyl-6,6-dimethyl-3,6-dihydro-2H- 1,3,4-thiadiazin-2-one;

5-[1-(N-phenyl-p-methoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-ethyl-p-chlorobenzimidoyl)-1,2,3,4-tetrahydroquinolin-6-yl]-3-ethyl-6,6-dimethyl-3,6-dihydro-2H-1,3,4-thiadiazin-2-one;

5-[1-(N-ethyl-2-thienylimidoyl)-1,2,3,4-tetrahydroquinolin-6-yl]-3-ethyl-6,6-dimethyl-3,6-dihydro-2H-1,3,4-thiadiazin-2-one;

5-[1-(N-(2-phenylethyl)-p-methoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-ethyl-o-methoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-ethyl-m-methoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-ethyl-2,4-dimethoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-methyl-p-methoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-ethyl-3,4-dichlorobenzimidoyl)-1,2,3,4-tetrahydroquinolin-6-yl]-3-ethyl-6,6-dimethyl-3,6-dihydro-2H-1,3,4-thiadiazin-2-one;

5-[1-(N-ethyl-2,4-dichlorobenzimidoyl)-1,2,3,4-tetrahydroquinolin-6-yl]-3-ethyl-6,6-dimethyl-3,6-dihydro-2H-1,3,4-thiadiazin-2-one;

5-[1-(N-isopropyl-p-methoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-cyclohexyl-p-methoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-isopropyl-p-chlorobenzimidoyl)-1,2,3,4-tetrahydroquinolin-6-yl]-3-ethyl-6,6-dimethyl-3,6-dihydro-2H-1,3,4-thiadiazin-2-one;

5-[1-(N-isopropyl-2-thienylimidoyl)-1,2,3,4-tetrahydroquinolin-6-yl]-3-ethyl-6,6-dimethyl-3,6-dihydro-2H-1,3,4-thiadiazin-2-one;

5-[1-(N-benzyl-p-methoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-isopropyl-o-methoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-isopropyl-m-methoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-isopropyl-2,4-dimethoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-cyclohexyl-p-methoxybenzimidoyl)-1,2,3,4-tetrahydroquinolin-6-yl]-3-ethyl-6,6-dimethyl-3,6-dihydro-2H-1,3,4-thiadiazin-2-one;

5-[1-(N-isopropyl-3,4-dichlorobenzimidoyl)-1,2,3,4-tetrahydroquinolin-6-yl]-3-ethyl-6,6-dimethyl-3,6-dihydro-2H-1,3,4-thiadiazin-2-one;

5-[1-(N-isopropyl-2,4-dichlorobenzimidoyl)-1,2,3,4-tetrahydroquinolin-6-yl]-3-ethyl-6,6-dimethyl-3,6-dihydro-2H-1,3,4-thiadiazin-2-one;

5-[1-(N-ethyl-p-methoxybenzimidoyl)-1,2,3,4-tetrahydroquinolin-6-yl]-3,6,6-trimethyl-6,6-dimethyl-3,6-dihydro-2H-1,3,4-thiadiazin-2-one;

5-[1-(N-phenyl-p-methoxybenzimidoyl)-1,2,3,4-tetrahydroquinolin-6-yl]-3,6,6-trimethyl-6,6-dimethyl-3,6-dihydro-2H-1,3,4-thiadiazin-2-one;

5-[1-(N-ethyl-p-nitrobenzimidoyl)-1,2,3,4-tetrahydroquinolin-6-yl]-3,6,6-trimethyl-3,6-dihydro-2H-1,3,4-thiadiazin-2-one;

5-[1-(N-ethyl-2-thienylimidoyl)-1,2,3,4-tetrahydroquinolin-6-yl]-3,6,6-trimethyl-3,6-dihydro-2H-1,3,4-thiadiazin-2-one;

5-[1-(N-(2-phenylethyl)-p-methoxybenzimidoyl)-1,2,3,4-tetrahydroquinolin-6-yl]-3,6,6-trimethyl-6,6-dimethyl-3,6-dihydro-2H-1,3,4-thiadiazin-2-one;

5-[1-(N-ethyl-o-methoxybenzimidoyl)-1,2,3,4-tetrahydroquinolin-6-yl]-3,6,6-trimethyl-3,6-dihydro-2H-1,3,4-thiadiazin-2-one;

5-[1-(N-ethyl-m-methoxybenzimidoyl)-1,2,3,4-tetrahydroquinolin-6-yl]-3,6,6-trimethyl-3,6-dihydro-2H-1,3,4-thiadiazin-2-one;

5-[1-(N-ethyl-3,4-dimethoxybenzimidoyl)-1,2,3,4-tetrahydroquinolin-6-yl]-3,6,6-trimethyl-3,6-dihydro-2H-1,3,4-thiadiazin-2-one;

5-[1-(N-methyl-p-methoxybenzimidoyl)-1,2,3,4-tetrahydroquinolin-6-yl]-3,6,6-trimethyl-3,6-dihydro-2H-1,3,4-thiadiazin-2-one;

5-[1-(N-ethyl-3,4-dichlorobenzimidoyl)-1,2,3,4-tetrahydroquinolin-6-yl]-3,6,6-trimethyl-3,6-dihydro-2H-1,3,4-thiadiazin-2-one;

5-[1-(N-isopropyl-2,4-dichlorobenzimidoyl)-1,2,3,4-tetrahydroquinolin-6-yl]-3,6,6-trimethyl-3,6-dihydro-2H-1,3,4-thiadiazin-2-one;

5-[1-(N-cyclohexyl-p-nitrobenzimidoyl)-1,2,3,4-tetrahydroquinolin-6-yl]-3,6,6-trimethyl-3,6-dihydro-2H-1,3,4-thiadiazin-2-one;

5-[1-(N-isopropyl-p-chlorobenzimidoyl)-1,2,3,4-tetrahydroquinolin-6-yl]-3,6,6-trimethyl-3,6-dihydro-2H-1,3,4-thiadiazin-2l-one;

5-[1-(N-isopropyl-2-thienylimidoyl)-1,2,3,4-tetrahydroquinolin-6-yl]-3,6,6-trimethyl-3,6-dihydro-2H-1,3,4-thiadiazin-2-one;

5-[1-(N-benzyl-p-methoxybenzimidoyl)-1,2,3,4-tetrahydroquinolin-6-yl]-3,6,6-trimethyl-3,6-dihydro-2H-1,3,4-thiadiazin-2-one;

5-[1-(N-isopropyl-o-methoxybenzimidoyl)-1,2,3,4-tetrahydroquinolin-6-yl]-3,6,6-trimethyl-3,6-dihydro-2H-1,3,4-thiadiazin-2-one;

5-[1-(N-isopropyl-m-methoxybenzimidoyl)-1,2,3,4-tetrahydroquinolin-6-yl]-3,6,6-trimethyl-3,6-dihydro-2H-1,3,4-thiadiazin-2-one;

5-[1-(N-isopropyl-2,4-dimethoxybenzimidoyl)-1,2,3,4-tetrahydroquinolin-6-yl]-3,6,6-trimethyl-3,6-dihydro-2H-1,3,4-thiadiazin-2-one;

5-[1-(N-cyclohexyl-p-methoxybenzimidoyl)-1,2,3,4-tetrahydroquinolin-6-yl]-3,6,6-trimethyl-3,6-dihydro-2H-1,3,4-thiadiazin-2-one;

5-[1-(N-isopropyl-2,4-dichlorobenzimidoyl)-1,2,3,4-tetrahydroquinolin-6-yl]-3,6,6-trimethyl-3,6-dihydro-2H-1,3,4-thiadiazin-2-one;

5-[1-(N-methyl-3,4-dimethoxybenzimidoyl)-1,2,3,4-tetrahydroquinolin-6-yl]-3,6,6-trimethyl-3,6-dihydro-2H-1,3,4-thiadiazin-2-one;

5-[1-(N-methyl-p-nitrobenzimidoyl)-1,2,3,4-tetrahydroquinolin-6-yl]-3,6,6-trimethyl-3,6-dihydro-2H-1,3,4-thiadiazin-2-one.

Example 7

A solution of 2.5 g of 5-[1-N-ethyl-3,4-dimethoxybenzimidoyl)-1,2,3,4-tetrahydroquinolin-6-yl]-6,6-dimethyl-3,6-dihydro-2H-1,3,4-thiadiazin-2-one (m.p. 188°) in 30 ml of dichloromethane is treated with 0.5 ml of triethylamine and then dropwise with stirring with 0.8 ml of acetyl chloride. The mixture is stirred for a further hour at room temperature and decomposed with water, and after customary working up 5-[1-N-ethyl-3,4-dimethoxybenzimidoyl)-1,2,3,4-tetrahydroquinolin-6-yl]-3-acetyl-6,6-dimethyl-3,6-dihydro-2H-1,3,4-thiadiazin-2-one is obtained.

The following are obtained analogously by acylation of the corresponding compounds of the formula I in the 3-position of the thiadiazinone system (formyl chloride is produced here by introducing CO and HCl gas into the reaction solution in the presence of $AlCl_3$ and CuCl):

5-[1-(N-ethyl-p-methoxybenzimidoyl)-1,2,3,4-tetrahydroquinolin-6-yl]-3-acetyl-6,6-dimethyl-3,6-dihydro-2H-1,3,4-thiadiazin-2-one;

5-[1-(N-phenyl-p-methoxybenzimidoyl)-1,2,3,4-tetrahydroquinolin-6-yl]-3-formyl-6,6-dimethyl-3,6-dihydro-2H-1,3,4-thiadiazin-2-one;

5-[1-(N-ethyl-p-chlorobenzimidoyl)-1,2,3,4-tetrahydroquinolin-6-yl]-3-acetyl-6,6-dimethyl-3,6-dihydro-2H-1,3,4-thiadiazin-2-one;

5-[1-(N-ethyl-2-thienylimidoyl)-1,2,3,4-tetrahydroquinolin-6-yl]-3-acetyl-6,6-dimethyl-3,6-dihydro-2H-1,3,4-thiadiazin-2-one;

5-[1-(N-(2-phenylethyl-p-methoxybenzimidoyl)-1,2,3,4-tetrahydroquinolin-6-yl]-3-formyl-6,6-dimethyl-3,6-dihydro-2H-1,3,4-thiadiazin-2-one;

5-[1-(N-ethyl-o-methoxybenzimidoyl)-1,2,3,4-tetrahydroquinolin-6-yl]-3-formyl-6,6-dimethyl-3,6-dihydro-2H-1,3,4-thiadiazin-2-one;

5-[1-(N-ethyl-m-methoxybenzimidoyl)-1,2,3,4-tetrahydroquinolin-6-yl]-3-acetyl-6,6-dimethyl-3,6-dihydro-2H-1,3,4-thiadiazin-2-one;

5-[1-(N-ethyl-2,4-dimethoxybenzimidoyl)-1,2,3,4-tetrahydroquinolin-6-yl]-3-acetyl-6,6-dimethyl-3,6-dihydro-2H-1,3,4-thiadiazin-2-one;

5-[1-(N-methyl-p-methoxybenzimidoyl)-1,2,3,4-tetrahydroquinolin-6-yl]-3-acetyl-6,6-dimethyl-3,6-dihydro-2H-1,3,4-thiadiazin-2-one;

5-[1-(N-ethyl-3,4-dichlorobenzimidoyl)-1,2,3,4-tetrahydroquinolin-6-yl]-3-acetyl-6,6-dimethyl-3,6-dihydro-2H-1,3,4-thiadiazin-2-one;

5-[1-(N-ethyl-2,4-dichlorobenzimidoyl)-1,2,3,4-tetrahydroquinolin-6-yl]-3-formyl-6,6-dimethyl-3,6-dihydro-2H-1,3,4-thiadiazin-2-one;

5-[1-(N-isopropyl-p-methoxybenzimidoyl)-1,2,3,4-tetrahydroquinolin-6-yl]-3-acetyl-6,6-dimethyl-3,6-dihydro-2H-1,3,4-thiadiazin-2-one;

5-[1-(N-isopropyl-p-chlorobenzimidoyl)-1,2,3,4-tetrahydroquinolin-6-yl]-3-acetyl-6,6-dimethyl-3,6-dihydro-2H-1,3,4-thiadiazin-2-one;

5-[1-(N-isopropyl-2-thienylimidoyl)-1,2,3,4-tetrahydroquinolin-6-yl]-3-acetyl-6,6-dimethyl-3,6-dihydro-2H-1,3,4-thiadiazin-2-one;

5-[1-(N-benzyl-p-methoxybenzimidoyl)-1,2,3,4-tetrahydroquinolin-6-yl]-3-acetyl-6,6-dimethyl-3,6-dihydro-2H-1,3,4-thiadiazin-2-one;

5-[1-(N-isopropyl-o-methoxybenzimidoyl)-1,2,3,4-tetrahydroquinolin-6-yl]-3-formyl-6,6-dimethyl-3,6-dihydro-2H-1,3,4-thiadiazin-2-one;

5-[1-(N-isopropyl-m-methoxybenzimidoyl)-1,2,3,4-tetrahydroquinolin-6-yl]-3-formyl-6,6-dimethyl-3,6-dihydro-2H-1,3,4-thiadiazin-2-one;

5-[1-(N-isopropyl-2,4-dimethoxybenzimidoyl)-1,2,3,4-tetrahydroquinolin-6-yl]-3-formyl-6,6-dimethyl-3,6-dihydro-2H-1,3,4-thiadiazin-2-one;

5-[1-(N-cyclohexyl-p-methoxybenzimidoyl)-1,2,3,4-tetrahydroquinolin-6-yl]-3-acetyl-6,6-dimethyl-3,6-dihydro-2H-1,3,4-thiadiazin-2-one;

5-[1-(N-isopropyl-3,4-dichlorobenzimidoyl)-1,2,3,4-tetrahydroquinolin-6-yl]-3-acetyl-6,6-dimethyl-3,6-dihydro-2H-1,3,4-thiadiazin-2-one;

5-[1-(N-isopropyl-2,4-dichlorobenzimidoyl)-1,2,3,4-tetrahydroquinolin-6-yl]-3-acetyl-6,6-dimethyl-3,6-dihydro-2H-1,3,4-thiadiazin-2-one;

5-[1-(N-ethyl-p-methoxybenzimidoyl)-1,2,3,4-tetrahydroquinolin-6-yl]-3-butyryl-6,6-dimethyl-3,6-dihydro-2H-1,3,4-thiadiazin-2-one;

5-[1-(N-phenyl-p-methoxybenzimidoyl)-1,2,3,4-tetrahydroquinol-6-yl]-3-butyryl-6,6-dimethyl-3,6-dihydro-2H-1,3,4-thiadiazin-2-one;

5-[1-(N-ethyl-p-chlorobenzimidoyl)-1,2,3,4-tetrahydroquinolin-6-yl]-3-propionyl-6,6-dimethyl-3,6-dihydro-2H-1,3,4-thiadiazin-2-one;

5-[1-(N-ethyl-2-thienylimidoyl)-1,2,3,4-tetrahydroquinolin-6-yl]-3-butyryl-6,6-dimethyl-3,6-dihydro-2H-1,3,4-thiadiazin-2-one;

5-[1-(N-(2-phenylethyl-p-methoxybenzimidoyl)-1,2,3,4-tetrahydroquinolin-6-yl]-3-propionyl-6,6-dimethyl-3,6-dihydro-2H-1,3,4-thiadiazin-2-one;

5-[1-(N-ethyl-o-methoxybenzimidoyl)-1,2,3,4-tetrahydroquinolin-6-yl]-3-isobutyryl-6,6-dimethyl-3,6-dihydro-2H-1,3,4-thiadiazin-2-one;

5-[1-(N-ethyl-m-methoxybenzimidoyl)-1,2,3,4-tetrahydroquinolin-6-yl]-3-isobutyryl-6,6-dimethyl-3,6-dihydro-2H-1,3,4-thiadiazin-2-one;

5-[1-(N-ethyl-2,4-dimethoxybenzimidoyl)-1,2,3,4-tetrahydroquinolin-6-yl]-3-butyryl-6,6-dimethyl-3,6-dihydro-2H-1,3,4-thiadiazin-2-one;

5-[1-(N-methyl-p-methoxybenzimidoyl)-1,2,3,4-tetrahydroquinolin-6-yl]-3-butyryl-6,6-dimethyl-3,6-dihydro-2H-1,3,4-thiadiazin-2-one;

5-[1-(N-ethyl-3,4-dichlorobenzimidoyl)-1,2,3,4-tetrahydroquinolin-6-yl]-3-propionyl-6,6-dimethyl-3,6-dihydro-2H-1,3,4-thiadiazin-2-one;

5-[1-(N-ethyl-2,4-dichlorobenzimidoyl)-1,2,3,4-tetrahydroquinolin-6-yl]-3-isobutyryl-6,6-dimethyl-3,6-dihydro-2H-1,3,4-thiadiazin-2-one;

5-[1-(N-isopropyl-p-methoxybenzimidoyl)-1,2,3,4-tetrahydroquinolin-6-yl]-3-isobutyryl-6,6-dimethyl-3,6-dihydro-2H-1,3,4thiadiazin-2-one;

5-[1-(N-cyclohexyl-p-methoxybenzimidoyl)-1,2,3,4-tetrahydroquinolin-6-yl]-3-isobutyryl-6,6-dimethyl-3,6-dihydro-2H-1,3,4-thiadiazin-2-one;

5-[1-(N-isopropyl-p-chlorobenzimidoyl)-1,2,3,4-tetrahydroquinolin-6-yl]-3-butyryl-6,6-dimethyl-3,6-dihydro-2H-1,3,4-thiadiazin-2one;

5-[1-(N-isopropyl-2-thienylimidoyl)-1,2,3,4-tetrahydroquinolin-6yl]-3-butyryl-6,6-dimethyl-3,6-dihydro-2H-1,3,4-thiadiazin-2-one;

5-[1-(N-benzyl-p-methoxybenzimidoyl)-1,2,3,4-tetrahydroquinolin-6-yl]-3-butyryl-6,6-dimethyl-3,6-dihydro-2H-1,3,4-thiadiazin-2-one;

5-[1-(N-isopropyl-o-methoxybenzimidoyl)-1,2,3,4-tetrahydroquinolin-6-yl]-3-butyryl-6,6-dimethyl-3,6-dihydro-2H-1,3,4-thiadiazin-2-one;

5-[1-(M-isopropyl-m-methoxybenzimidoyl)-1,2,3,4-tetrahydroquinolin-6-yl]-3-butyryl-6,6-dimethyl-3,6-dihydro-2H-1,3,4-thiadiazin-2-one;

5-[1-(N-isopropyl-2,4-dimethoxybenzimidoyl)-1,2,3,4-tetrahydroquinolin-6-yl]-3-butyryl-6,6-dimethyl-3,6-dihydro-2H-1,3,4-thiadiazin-2-one;

5-[1-(N-cyclohexyl-p-methoxybenzimidoyl)-1,2,3,4-tetrahydroquinolin-6-yl]-3-butyryl-6,6-dimethyl-3,6-dihydro-2H-1,3,4-thiadiazin-2-one;

5-[1-(N-isopropyl-3,4-dichlorobenzimidoyl)-1,2,3,4-tetrahydroquinolin-6-yl]-3-propionyl-6,6-dimethyl-3,6-dihydro-2H-1,3,4-thiadiazin-2-one;

5-[1-(N-isopropyl-2,4-dichlorobenzimidoyl)-1,2,3,4-tetrahydroquinolin-6-yl]-3-isobutyryl-6,6-dimethyl-3,6-dihydro-2H-1,3,4-thiadiazin-2-one.

Example 8

5-[1-(n-(p-methanesulfonamidophenyl)-3,4-dimethoxybenzimidoyl)-1,2,3,4-tetrahydroquinolin-6-yl]-3,6,6-trimethyl-3,6-dihydro-2H-1,3,4-thiadiazin-2-one is obtained analogously to Example 1 starting from 5-(1,2,3,4-tetrahydroquinolin-6-yl)-3,6,6-trimethyl-3,6-dihydro-1,3,4-thiadiazin-2-one ("B") [obtainable from O-ethyl N-methylhydrazinothioformate and 6-(2-chloro-2-methylpropionyl)-2-oxo-1,2,3,4-tetrahydroquinoline] by reaction with N-[1-N-(p-methanesulfonamidophenyl)-3,4-dimethoxybenzimidoyl chloride.

The following are obtained analogously:

starting from "B" by reaction with N-(p-methanesulfonamidophenyl)-4-nitrobenzimidoyl chloride: 5-[1-(N-(p-methanesulfonamidophenyl)-4-nitrobenzimidoyl)-1,2,3,4-tetrahydroquinolin-6-yl]-3,6,6-trimethyl-3,6-dihydro-2H-1,3,4-thiadiazin-2-one;

with N-(P-methanesulfonamidophenyl)-4-cyanobenzimidoyl chloride: 5-[1-(N-(p-methanesulfonamidophenyl)-4-cyanobenzimidoyl)-1,2,3,4-tetrahydroquinolin-6-yl]-3,6,6-trimethyl-3,6-dihydro-2H-1,3,4-thiadiazin-2-one;

with N-(p-methanesulfonamidophenyl)-3,4-dimethoxybenzimidoyl chloride: 5-[1-(N-(p-methanesulfonamidophenyl)-3,4-dimethoxybenzimidoyl)-1,2,3,4-tetrahydroquinolin-6-yl]-3,6,6-trimethyl-3,6-dihydro-2H-1,3,4-thiadiazin-2-one;

with N-(p-methanesulfonamidophenyl)-4-methanesulfonamidobenzimidoyl chloride: 5-[1-(N-(p-methanesulfonamidophenyl)-4-methanesulfonamidobenzimidoyl)-1,2,3,4-tetrahydroquinolin-6-yl]-3,6,6-trimethyl-3,6-dihydro-2H-1,3,4-thiadiazin-2-one;

with N-(p-methanesulfonamidophenyl)-4-nitrobenzimidoyl chloride: 5-[1-(N-(p-methanesulfonamidobenzyl)-4-nitrobenzimidoyl)-1,2,3,4-tetrahydroquinolin-6-yl]-3,6,6-trimethyl-3,6-dihydro-2H-1,3,4-thiadiazin-2-one;

with N-(p-methanesulfonamidobenzyl)-4-cyanobenzimidoyl chloride: 5-[1-(N-(p-methanesulfonamidobenzyl)-4-cyano benzimidoyl)-1,2,3,4-tetrahydroquinolin-6-yl]-3,6,6-trimethyl-3,6-dihydro-2H-1,3,4-thiadiazin-2-one;

with N-(p-methanesulfonamidobenzyl)-3,4-dimethoxybenzimidoyl chloride: 5-[1-(N-(p-methanesulfonamidobenzyl)-3,4-dimethoxybenzimidoyl)-1,2,3,4-tetrahydroquinolin-6-yl]-3,6,6-trimethyl-3,6-dihydro-2H-1,3,4-thiadiazin-2-one;

with N-(p-methanesulfonamidobenzyl)-4-methanesulfonamidobenzimidoyl chloride: 5-[1-(N-(p-methanesulfonamidobenzyl)-4-methanesulfonamidobenzimidoyl)-1,2,3,4-tetrahydroquinolin-6-yl]-3,6,6-trimethyl-3,6-dihydro-2H-1,3,4-thiadiazin-2-one;

with N-[2-(p-methanesulfonamidophenyl)ethyl]-4-nitrobenzimidoyl chloride: 5-[1-(N-(2-p-methanesulfonamidophenyl)ethyl)-4-nitrobenzimidoyl)-1,2,3,4-tetrahydroquinolin-6-yl]-3,6,6-trimethyl-3,6-dihydro-2H-1,3,4-thiadiazin-2-one;

with N-[2-[2-(p-methanesulfonamidophenyl)ethyl]-4-cyanobenzimidoyl chloride 5-[1-(N-(2-(p-methanesulfonamidophenyl)ethyl)-4-cyanobenzimidoyl)-1,2,3,4-tetrahydroquinolin-6-yl]-3,6,6-trimethyl-3,6-dihydro-2H-1,3,4-thiadiazin-2-one;

with N-[2-(p-methanesulfonamidophenyl)ethyl]-3,4-dimethoxybenzimidoyl chloride: 5-[1-(N-(2-p-methanesulfonamidophenyl)ethyl]-3,4-dimethoxybenzimidoyl)-1,2,3,4-tetrahydroquinolin-6-yl]-3,6,6-trimethyl-3,6-dihydro-2H-1,3,4-thiadiazin-2-one;

with N-[2-(p-methanesulfonamidophenyl)ethyl]-4-methanesulfonamidobenzimidoyl chloride: 5-[1-(N-(2-(p-methanesulfonamidophenyl)ethyl)-4-methanesulfonamidobenzimidoyl)-1,2,3,4-tetrahydroquinolin-6-yl]-3,6,6-trimethyl-3,6-dihydro-2H-1,3,4-thiadiazin-2-one.

Example 9

5-[1-N-(p-Methanesulfonamidophenyl)-3,4-dimethoxybenzimidoyl)-1,2,3,4-tetrahydroquinolin-6-yl]-3-methyl-3,6-dihydro-2H-1,3,4-thiadiazin-2-one is obtained analogously to Example 1 starting from 5-(1,2,3,4-tetrahydroquinolin-6-yl)-3-methyl-3,6-dihydro-1,3,4-thiadiazin-2-one ("C") [obtainable from O-ethyl 1-methylhydrazinothioformate and 6-chloroacetyl-1,2,3,4-tetrahydroquinoline] by reaction with N-(p-methanesulfonamidophenyl)-3,4-dimethoxybenzimidoyl chloride.

The following are obtained analogously:

starting from "C" by reaction
with N-(p-methanesulfonamidophenyl)-4-nitrobenzimidoyl chloride: 5-[1-(N-(p-methanesulfonamidophenyl)-4-nitrobenzimidoyl)-1,2,3,4-tetrahydroquinolin-6-yl]-3-methyl-3,6-dihydro-2H-1,3,4-thiadiazin-2-one;

with N-(p-methanesulfonamidophenyl)-4-cyanobenzimidoyl chloride: 5-[1-(N-(p-methanesulfonamidophenyl)-4-cyanobenzimidoyl)-1,2,3,4-tetrahydroquinolin-6-yl]-3-methyl-3,6-dihydro-2H-1,3,4-thiadiazin-2-one;

with N-(p-methanesulfonamidophenyl)-4-methanesulfonamidobenzimidoyl chloride: 5-[1-(N-(p-methanesulfonamidophenyl)-4-methanesulfonamidobenzimidoyl)-1,2,3,4-tetrahydroquinolin-6-yl]-3-methyl-3,6-dihydro-2H-1,3,4-thiadiazin-2-one;

with N-(p-methanesulfonamidophenylbenzyl)-4-nitrobenzimidoyl chloride: 5-[1-(N-(p-methanesulfonamidobenzyl)-4-nitrobenzimidoyl)-1,2,3,4-tetrahydroquinolin-6-yl]-3-methyl-3,6-dihydro-2H-1,3,4-thiadiazin-2-one;

with N-(p-methanesulfonamidobenzyl)-4-cyanobenzimidoyl chloride: 5-[1-(N-(p-methanesulfonamidobenzyl)-4-cyanobenzimidoyl)-1,2,3,4-tetrahydroquinolin-6-yl]-3-methyl-3,6-dihydro-2H-1,3,4-thiadiazin-2-one;

with N-(p-methanesulfonamidobenzyl)-3,4-dimethoxybenzimidoyl chloride: 5-[1-(N-(p-methanesulfonamidobenzyl)-3,4-dimethoxybenzimidoyl)-1,2,3,4-tetrahydroquinolin-6-yl]-3-methyl-3,6-dihydro-2H-1,3,4-thiadiazin-2-one;

with N-(p-methanesulfonamidobenzyl)-4-methanesulfonamidobenzimidoyl chloride: 5-[1-(N-(p-methanesulfonamidobenzyl)-4-methanesulfonamidobenzimidoyl)-1,2,3,4-tetrahydroquinolin-6-yl]-3-methyl-3,6-dihydro-2H-1,3,4-thiadiazin-2-one;

with N-[2-(p-methanesulfonamidophenyl)ethyl]-4-nitrobenzimidoyl chloride: 5-[1-(N-(2-(p-methanesulfonamidophenyl)ethyl)-4-nitrobenzimidoyl)-1,2,3,4-tetrahydroquinolin-6-yl]-3-methyl-3,6-dihydro-2H-1,3,4-thiadiazin-2-one;

with N-[2-(p-methanesulfonamidophenyl)ethyl]-4-cyanobenzimidoyl chloride: 5-[1-(N-(2-(p-methanesulfonamidophenyl)ethyl)-4-cyanobenzimidoyl)-1,2,3,4-tetrahydroquinolin-6-yl]-3-methyl-3,6-dihydro-2H-1,3,4-thiadiazin-2-one;

with N-[2-(p-methanesulfonamidophenyl)ethyl]-3,4-dimethoxybenzimidoyl chloride: 5-[1-(N-(2-(p-methanesulfonamidophenyl)ethyl)-3,4-dimethoxybenzimidoyl)-1,2,3,4-tetrahydroquinolin-6-yl]-3-methyl-3,6-dihydro-2H-1,3,4-thiadiazin-2-one;

with N-[2-(p-methanesulfonamidophenyl)ethyl]-4-methanesulfonamidobenzimidoyl chloride: 5-[1-(N-(2-(p-methanesulfonamidophenyl)ethyl)-4-methanesulfonamidobenzimidoyl)-1,2,3,4-tetrahydroquinolin-6-yl]-3-methyl-3,6-dihydro-2H-1,3,4-thiadiazin-2-one;

with N-methyl-4-nitrobenzimidoyl chloride: 5-[1-(N-methyl-4-nitrobenzimidoyl)-1,2,3,4-tetrahydroquinolin-6-yl]-3-methyl-3,6-dihydro-2H-1,3,4-thiadiazin-2-one;

with N-methyl-4-cyanobenzimidoyl chloride: 5-[1-(N-methyl-4-cyanobenzimidoyl)-1,2,3,4-tetrahydroquinolin-6-yl]-3-methyl-3,6-dihydro-2H-1,3,4-thiadiazin-2-one;

with N-methyl-3,4-dimethoxybenzimidoyl chloride: 5-[1-(N-methyl-3,4-dimethoxybenzimidoyl)-1,2,3,4-tetrahydroquinolin)-6-yl]-3-methyl-3,6-dihydro-2H-1,3,4-thiadiazin-2-one;

with N-methyl-4-methanesulfonamidobenzimidoyl chloride: 5-[1-(N-methyl-4-methanesulfonamidobenzimidoyl)-1,2,3,4-tetrahydroquinolin-6-yl]-3-methyl-3,6-dihydro-2H-1,3,4-thiadiazin-2-one;

with N-ethyl-4-nitrobenzimidoyl chloride: 5-[1-(N-ethyl-4-nitrobenzimidoyl)-1,2,3,4-tetrahydroquinolin-6-yl]-3-methyl-3,6-dihydro-2H-1,3,4-thiadiazin-2-one;

with N-ethyl-4-cyanobenzimidoyl chloride: 5-[1-(N-ethyl-4-cyanobenzimidoyl)-1,2,3,4-tetrahydroquinolin-6-yl]-3-methyl-3,6-dihydro-2H-1,3,4-thiadiazin-2-one;

with N-ethyl-3,4-dimethoxybenzimidoyl chloride: 5-[1-(N-ethyl-3,4-dimethoxybenzimidoyl)-1,2,3,4-tetrahydroquinolin-6-yl]-3-methyl-3,6-dihydro-2H-1,3,4-thiadiazin-2-one;

with N-ethyl-4-methanesulfonamidobenzimidoyl chloride: 5-[1-(N-ethyl-4-methanesulfonamidobenzimidoyl)-1,2,3,4-tetrahydroquinolin-6-yl]-3-methyl-3,6-dihydro-2H-1,3,4-thiadiazin-2-one.

Example 10

5-[1-(N-Ethyl-3,4-dimethoxybenzimidoyl)-2,3-dihydroindol-5-yl]-3,6,6-trimethyl-3,6-dihydro-2H-1,3,4-thiadiazin-2-one is obtained analogously to Example 1 starting from 5-(2,3-dihydroindol-5-yl)3,6,6-trimethyl-3,6-dihydro-1,3,4-thiadiazin-2-one ("D") by reaction with N-ethyl-3,4-dimethoxybenzimidoyl chloride.

The following are obtained analogously:

starting from "D" by reaction with N-ethyl-4-nitrobenzimidoyl chloride: 5-[1-(N-ethyl-4-nitrobenzimidoyl)-2,3-dihydroindol-5-yl]-3,6,6-trimethyl-3,6-dihydro-2H-1,3,4-thiadiazin-2-one;

with N-ethyl-4-cyanobenzimidoyl chloride: 5-[1-(N-ethyl-4-cyanobenzimidoyl)-2,3-dihydroindol-5-yl]-3,6,6-trimethyl-3,6-dihydro-2H-1,3,4-thiadiazin-2-one;

with N-ethyl-3,4-dimethoxybenzimidoyl chloride: 5-[1-(N-ethyl-3,4-dimethoxybenzimidoyl)-2,3-dihydroindol-5-yl]-3,6,6-trimethyl-3,6-dihydro-2H-1,3,4-thiadiazin-2-one;

with N-ethyl-4-methanesulfonamidobenzimidoyl chloride: 5-[1-(N-ethyl-4-methanesulfonamidobenzimidoyl)-2,3-dihydroindol-5-yl]-3,6,6-trimethyl-3,6-dihydro-2H-1,3,4-thiadiazin-2-one;

The following are obtained analogous starting from 5-(2,3-dihydroindol-5-yl)-6,6-dimethyl-3,6-dihydro-1,3,4- thiadiazin-2-one by reaction with N-ethyl-4-nitrobenzimidoyl chloride:
5-[1-(N-ethyl-4-nitrobenzimidoyl)-2,3-dihydroindol-5-yl]-6,6-dimethyl-3,6-dihydro-2H-1,3,4-thiadiazin-2-one;

with N-ethyl-4-cyanobenzimidoyl chloride: 5-[1-(N-ethyl-4-cyanobenzimidoyl)-2,3-dihydroindol-5-yl]-6,6-dimethyl-3,6-dihydro-2H-1,3,4-thiadiazin-2-one;

with N-ethyl-3,4-dimethoxybenzimidoyl chloride: 5-[1-(N-ethyl-3,4-dimethoxybenzimidoyl)-2,3-dihydroindol-5yl]-6,6-dimethyl-3,6-dihydro-2H-1,3,4-thiadiazin-2-one;

with N-ethyl-4-methanesulfonamidobenzimidoyl chloride: 5-[1-(N-ethyl-4-methanesulfonamidobenzimidoyl)-2,3-dihydroindol-5-yl]-6,6-dimethyl-3,6-dihydro-2H-1,3,4-thiadiazin-2-one.

Example 11

5-[1-(N-Ethyl-3,4-dimethoxybenzimidoyl)-1,2,3,4-tetrahydroquinolin-6-yl]-3-carbomethoxy-3,6-dihydro-2H-1,3,4-thiadiazin-2-one is obtained analogously to Example 1 starting from 5-(1,2,3,4-tetrahydroquinolin-6-yl)-3-carbomethoxy-3,6-dihydro-1,3,4-thiadiazin-2-one ("E") by reaction with N-ethyl-3,4-dimethoxybenzimidoyl chloride.

The following are obtained analogously:
starting from "E" by reaction with N-ethyl-4-nitrobenzimidoyl chloride: 5-[1-(N-ethyl-4-nitrobenzimidoyl)-1,2,3,4-tetrahydroquinolin-6-yl]-3-carbomethoxy-3,6-dihydro-2H-1,3,4-thiadiazin-2-one:

with N-ethyl-4-cyanobenzimidoyl chloride: 5-[1-(N-ethyl-4-cyanobenzimidoyl)-1,2,3,4-tetrahydroquinolin-6-yl]-3-carbomethoxy-3,6-dihydro-2H-1,3,4-thiadiazin-2-one;

with N-ethyl-2,4-dimethoxybenzimidoyl chloride: 5-[1-(N-ethyl-2,4-dimethoxybenzimidoyl)-1,2,3,4-tetrahydroquinolin-6-yl]-3-carbomethoxy-3,6-dihydro-2H-1,3,4-thiadiazin-2-one;

with N-ethyl-4-methanesulfonamidobenzimidoyl chloride: 5-[1-(N-ethyl-4-methanesulfonamidobenzimidoyl)-1,2,3,4-tetrahydroquinolin-6-yl]-3-carbomethoxy-3,6-dihydro-2H-1,3,4-thiadiazin-2-one.

Example 12

5-[1-(N-Ethyl-3,4-dimethoxybenzimidoyl)-1,2,3,4-tetrahydroquinolin-6-yl]-3-carbomethoxy-6,6-dimethyl-3,6-dihydro-2H-1,3,4-thiadiazin-2-one is obtained analogously to Example 1 starting from 5-(1,2,3,4-tetrahydroquinolin-6-yl)-3-carbomethoxy-6,6-dimethyl-3,6-dihydro-1,3,4-thiadiazin-2-one ("F") by reaction with N-ethyl-3,4-dimethoxybenzimidoyl chloride.

The following are obtained analogously:
starting from "F" by reaction with N-ethyl-4-nitrobenzimidoyl chloride: 5-[1-(N-ethyl-4-nitrobenzimidoyl)-1,2,3,4-tetrahydroquinolin-6-yl]-3-carbomethoxy-6,6-dimethyl-3,6-dihydro-2H-1,3,4-thiadiazin-2-one;

with N-ethyl-4-cyanobenzimidoyl chloride: 5-[1-(N-ethyl-4-cyanobenzimidoyl)-1,2,3,4-tetrahydroquinolin-6-yl]-3-carbomethoxy-6,6-dimethyl-3,6-dihydro-2H-1,3,4-thiadiazin-2-one;

with N-ethyl-2 , 4-dimethoxybenzimidoyl chloride: 5-[1-(N-ethyl-2,4-dimethoxybenzimidoyl)-1,2,3,4-tetrahydroquinolin-6-yl]-3-carbomethoxy-6,6-dimethyl-3,6-dihydro-2H-1,3,4-thiadiazin-2-one;

with N-ethyl-4-methanesulfonamidobenzimidoyl chloride: 5-[1-(N-ethyl-4-methanesulfonamidobenzimidoyl)-1,2,3,4-tetrahydroquinolin-6-yl]-3-carbomethoxy-6,6-dimethyl-3,6-dihydro-2H-1,3,4-thiadiazin-2-one.

The examples below relate to pharmaceutical preparations which contain compounds of the formula I or their acid addition salts.

Example A

Tablets

A mixture of 1 kg of 5-[1-(N-ethyl-3,4-dimethoxybenzimidoyl)-1,2,3,4-tetrahydroquinolin-6-yl]-6,6-dimethyl-3,6-dihydro-2H-1,3,4-thiadiazin-2-one, 10 kg of lactose, 6 kg of microcrystalline cellulose, 6 kg of potato starch, 1 kg of polyvinylpyrrolidone, 0.8 g of talc and 0.1 kg of magnesium stearate is pressed in a customary manner to give tablets in such a way that each tablet contains 10 mg of active substance.

Example B

Coated Tablets

Analogously to Example A, tablets are pressed which are then coated in a customary manner with a coating of sucrose, potato starch, talc, tragacanth and colorant.

Example C

Capsules 1 kg of 5-[1-(N-isopropyl-3,4-dimethoxybenzimidoyl)-1,2,3,4-tetrahydroquinolin-6-yl)-6,6-dimethyl-3,6-dihydro-2H-1,3,4-thiadiazin-2-one is filled in a customary manner into hard gelatine capsules such that each capsule contains 5 mg of active substance.

Example D

Ampoules

A solution of 1 kg of 5-[1-(N-ethyl-p-fluorobenzimidoyl)-1,2,3,4-tetrahydroquinolin-6-yl]-6,6-dimethyl-3,6-dihydro-2H-1,3,4-thiadiazin-2-one in 30 l of 1,2-propanediol is sterile-filtered, filled into ampoules and sealed under sterile conditions. Each ampoule contains 2 mg of active substance.

Analogously obtainable are tablets, coated tablets, capsules and ampoules which contain one of the other active substances of the formula I and/or their physiologically acceptable acid addition salts.

The compounds can also be used for the preparation of other formulations and administration forms.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A thiadiazinone compound of formula I

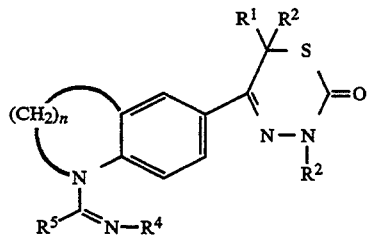

wherein $R^1$ and $R^2$ in each case independently of one another are A;

$R^3$ is H, A or Ac;

$R^4$ is H, A, cycloalkyl having 3–7 C atoms, Ar or Ar—alk;

$R^5$ is Ar or Het;

A is alkyl having 1–8 C atoms;

Ac is A—CO—, Ar—CO—, Ar—alk—CO—, A—O—CO— or A—NH—CO—;

—alk is alkylene having 1–5 C atoms;

Ar is an unsubstituted phenyl radical or a phenyl radical which is mono-, di- or trisubstituted by A, OH, OA, F, Cl, Br, I, SA, SOA, $SO_2A$, $NH_2$, NHA, $NA_2$, NHAc, $NHSO_2A$, CN or $NO_2$;

Het is a thienyl or pyridyl group, which can be mono- or disubstituted by A, OA, F, Cl, Br, I, OH, $NO_2$, $NH_2$, NHA, $NA_2$, NHAc, NH—$SO_2$—A, SO—A, $SO_2$—A, $SO_2$—A, $SO_2NH_2$ and/or $SO_2NHA$;

n is 2, 3 or 4;

or a salt thereof.

2. A compound according to claim 1, which is (a) 5-[1-(N-ethyl-4-methoxybenzimidoyl)-1,2,3,4-tetrahydroquinolin-6-yl]-6,6-dimethyl-3,6-dihydro-2H-1,3,4-thiadiazin-2-one;

(b) 5-[1-(N-phenylbenzimidoyl)-1,2,3,4-tetrahydroquinolin-6-yl]-6,6-dimethyl-3,6-dihydro-2H-1,3,4-thiadiazin-2-one; or (c) 5-[1-(N-ethyl-4-chlorobenzimidoyl)-1,2,3,4-tetrahydroquinolin-6-yl]-6,6-dimethyl-3,6-dihydro-2H-1,3,4-thiadiazin-2-one;

(d) 5-[1-(N-2-phenylethyl)-3,4-dimethoxybenzimidoyl)-1,2,3,4-tetrahydroquinolin-6-yl]-6,6-dimethyl-3,6-dihydro-2H-1,3,4-thiadiazin-2-one; or (e) 5-[1-(N-ethyl-2-thienylimidoyl)-1,2,3,4-tetrahydroquinolin-6-yl]-6,6-dimethyl-3,6-dihydro-2H-1,3,4-thiadiazin-2-one.

3. A process for the preparation of a thiadiazinone of the formula I according to claim 1, or a salt thereof, comprising reacting a ketone of the formula IV

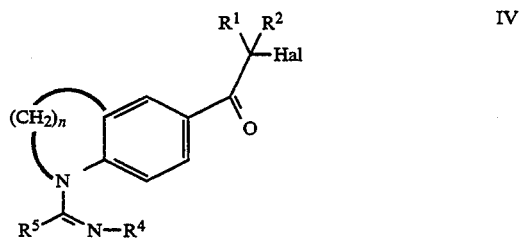

in which $R^1$, $R^2$, $R^4$, $R^5$ and n have the meanings given in claim 1; and Hal is Cl, Br or I, is reacted with a compound of the formula V

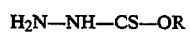

$H_2N$—NH—CS—OR    V in which

R is alkyl having 1–5 C atoms or an equivalent of a metal or ammonium cation.

4. A compound according to claim 1, wherein n is 3;

$R^1$, $R^2$ and $R^3$ are in each case independently of one another H or methyl;

$R^4$ is $C_{1-5}$-alkyl; and $R^5$ is monosubstituted or disubstituted phenyl.

5. A compound according to claim 1, wherein n is 3;

$R^1$, $R^2$ and $R^3$ are in each case independently of one another H or methyl;

$R^4$ is phenyl; and $R^5$ is unsubstituted, monosubstituted or disubstituted phenyl.

6. A compound according to claim 1, wherein n is 3;

$R^1$, $R^2$ and $R^3$ are in each case independently of one another H or methyl;

$R^4$ is ethyl; and $R^5$ is monosubstituted or disubstituted phenyl.

7. A compound according to claim 1, wherein n is 3;

$R^1$, $R^2$ and $R^3$ are in each case independently of one another H or methyl;

$R^4$ is alkyl having 1–5 C atoms; and $R^5$ is phenyl, p-nitrophenyl, p-cyanophenyl, p-methane-sulfonamidophenyl, p-chlorophenyl, p-methoxyphenyl, 3,4-dimethoxyphenyl or 2-thienyl.

8. A compound according to claim 1, wherein n is 3;

$R^1$, $R^2$ and $R^3$ are in each case independently of one another H or methyl;

$R^4$ is benzyl or 2-phenylethyl; and $R^5$ is phenyl, p-nitrophenyl, p-cyanophenyl, p-methane-sulfonamidophenyl, p-chlorophenyl, p-methoxyphenyl, 3,4-dimethoxyphenyl or 2-thienyl.

9. A compound according to claim 1, wherein n is 3;

$R^1$, $R^2$ and $R^3$ are in each case independently of one another H or methyl;

$R^4$ is ethyl; and $R^5$ is 2-thienyl, p-nitrophenyl, p-cyanophenyl or p-methanesulfonamidophenyl.

10. A compound according to claim 1, which is (a) 5-[1-(N-ethyl-3,4-dimethoxy-benzimidoyl)-1,2,3,4-tetrahydroquinolin-6-yl]-6,6-dimethyl-3,6-dihydro-2H-1,3,4-thiadiazin-2-one;

(b) 5-[1-(N-isopropyl-3,4-dimethoxy-benzimidoyl)-1,2,3,4-tetrahydroquinolin-6-yl]-6,6-dimethyl-3,6-dihydro-2H-1,3,4-thiadiazin-2-one; or (c) 5-[1-(N-ethyl-p-fluoro-benzimidoyl)-1,2,3,4-tetrahydroquinolin-6-yl]-6,6-dimethyl-3,6-dihydro-2H-1,3,4-thiadiazin-2-one.

11. A pharmaceutical composition comprising a compound according to claim 1 and physiologically acceptable excipient.

12. A pharmaceutical composition comprising a compound according to claim 2 and physiologically acceptable excipient.

13. A pharmaceutical composition comprising a compound according to claim 4.

14. A pharmaceutical composition comprising a compound according to claim 10.

15. The pharmaceutical composition according to claim 11 which is a tablet or a capsule.

16. A method of treating cardiac insufficiency or arrhythmia comprising administering an effective amount of a compound according to claim 1.

17. A method of claim 16, wherein the compound is administered in an amount of 1–100 mg.

18. A method of claim 16, wherein the compound is administered in an amount of 2–20 mg.

* * * * *